United States Patent [19]
Fujiwara et al.

[11] Patent Number: 5,281,752
[45] Date of Patent: Jan. 25, 1994

[54] PROCESS FOR PRODUCING CARBOXYLIC ACIDS

[75] Inventors: Yuzo Fujiwara, Higashihiroshima; Ken Takaki, Aki, both of Japan

[73] Assignee: Sumitomo Chemical Company, Limited, Osaka, Japan

[21] Appl. No.: 26,825

[22] Filed: Mar. 8, 1993

[30] Foreign Application Priority Data

Mar. 9, 1992 [JP] Japan .................................. 4-050610
Apr. 16, 1992 [JP] Japan .................................. 4-096429

[51] Int. Cl.$^5$ ...................... C07C 51/14; C07C 51/10
[52] U.S. Cl. .................................. 562/522; 562/517; 562/521
[58] Field of Search ............... 562/522, 517, 519, 521

[56] References Cited

U.S. PATENT DOCUMENTS

| | | | |
|---|---|---|---|
| 2,874,186 | 2/1959 | Friedman | 260/514 |
| 3,910,963 | 10/1975 | Souma et al. | 562/517 X |
| 4,093,647 | 6/1978 | van Venrooy | 260/515 R |
| 4,547,590 | 10/1985 | Love et al. | 562/517 X |
| 4,665,213 | 5/1987 | Alper et al. | 562/522 X |
| 4,681,707 | 7/1987 | Alper et al. | 562/522 X |
| 5,041,642 | 8/1991 | Jenck | 562/522 |

OTHER PUBLICATIONS

H. Hogeveen et al. "Trapping of the Methyl Cation by Carbon by Carbon Monoxide; Formation of Acetic Acid from Mrthane", Journal of the Chemical Society, No. 16 Aug. 1969, pp. 920-921.
"Pd-Catalyzed Regio-and Stereo-selective Carboxylation of Cycloalkanes with CO", Chem. Letters, Chem. Soc. Japan Satoh, Koichi et al., pp. 1433-1436 (1991).
"Palladium Catalyzed Carboxylation of Cyclohexane with Carbon Monoxide", Chem. Letters, Chem. Soc. Japan, Nakata, K. et al., pp. 1437-1438 (1991).

*Primary Examiner*—Arthur C. Prescott
*Attorney, Agent, or Firm*—Cushman, Darby & Cushman

[57] ABSTRACT

Lower carboxylic acids such as acetic acid, are produced efficiently from inexpensive lower alkanes such as methane by allowing the lower alkanes to react with carbon monoxide in the presence of palladium and/or copper catalysts and salts of peroxy acids.

12 Claims, No Drawings

PROCESS FOR PRODUCING CARBOXYLIC ACIDS

The present invention relates to a process for producing lower carboxylic acids and in particular, to a process for producing lower carboxylic acids which comprises allowing lower alkanes to react with carbon monoxide in the presence of palladium and/or copper catalysts and salts of peroxy acids.

As processes for producing lower carboxylic acids, there have been known a process of oxidizing the corresponding aldehydes, alkanes, alkenes or the like and a process of carbonylation of methanol to produce acetic acid. However, production of lower carboxylic acids from lower alkanes and carbon monoxide has never been known.

The inventors have conducted intensive research on the reaction of alkanes with carbon monoxide and found that lower alkanes react with carbon monoxide in the presence of palladium and/or copper catalysts and salts of peroxy acids to give lower carboxylic acids. After further study, they have accomplished the present invention.

That is, the present invention provides a process for producing lower carboxylic acids which comprises allowing lower alkanes to react with carbon monoxide in the presence of palladium and/or copper catalysts and salts of peroxy acids.

The present invention will be explained in detail.

As the palladium catalysts, mention may be made of salts of palladium such as acetylacetonato salt, carboxylates, oxides, halides, ammonium salts, sulfates and nitrates and coordination compounds thereof. Typical examples are $Pd(NH_3)_2(NO_2)_2$, $Pd(NH_3)_2Br_2$, $Pd(NH_3)_2Cl_2$, $PdCl_2(CH_3CN)$, $PdCl_2(PhCN)$, $PdCl_2(1,5-C_8H_{12})$, $Pd(O_2CCH_3)_2$, $Pd(O_2CC_3H_7)_2$, $Pd(CH_3COCHCOCH_3)_2$, $PdBr_2$, $PdCl_2$, $PdI_2$, $Pd(CN)_2$, $Pd(NO_3)_2 \cdot xH_2O$, $PdO$, $Pd(OCOC_2H_5)_2$, $PdSO_4 \cdot 2H_2O$, $Pd(O_2CCF_3)_2 \cdot [Pd(NH_3)_4](NO_3)_2$, $[Pd(NH_3)_4][PdCl_4]$, $Pd(CH_3CN)(BF_4)_2$, $PdCl_2[(Ph)_3P]_2$, and $Pd[(Ph)_3 P]_4$. Among them, $Pd(O_2CCH_3)_2$, $Pd(O_2CC_2H_5)_2$, $Pd(O_2CC_3H_7)_2$ and $PdCl_2$ are preferred.

As the copper catalysts, mention may be made of oxides, halides, hydroxides, carboxylates, sulfates, nitrates and carbonates of copper. Typical examples are cuprous oxide, cupric oxide, cuprous chloride, cupric chloride, cuprous bromide, cupric bromide, cuprous iodide, cupric iodide, copper hydroxide, copper acetate, copper oxalate, copper formate, copper naphthenate, copper stearate, copper sulfate, copper nitrate and copper carbonate. Copper acetate and copper sulfate are preferred.

The palladium catalysts and the copper catalysts may be used in combination. Amount of the catalyst used is usually about $1 \times 10^{-5} - 1 \times 10^{-1}$ mol per mol of the alkane.

The salts of peroxy acids include, for example, salts of peroxysulfuric acid and salts of peroxyphosphoric acid. Typical examples are ammonium peroxydisulfate, sodium peroxydisulfate, potassium peroxydisulfate and potassium peroxydiphosphate. The amount of the salts is usually 50-200 molar equivalents based on the catalyst.

Furthermore, trivalent phosphorus compounds may also be present. When alkanes of 3 or more carbon atoms are used, distribution of the products is changed. For example, when propane is used, proportion of the iso-form products is increased. As examples of the trivalent phosphorus compounds, mention may be made of the compounds represented by the following formulas:

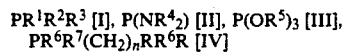

(wherein $R^1$, $R^2$, $R^3$, $R^4$, $R^5$, $R^6$ and $R^7$ each represents an alkyl group, a cycloalkyl group, an aralkyl group or an aryl group). More specific examples of the compounds are phosphines represented by the formula [I] such as trimethylphosphine, triethylphosphine, tri-n-propylphosphine, triisopropylphosphine, tri-n-butylphosphine, triisobutylphosphine, tri-t-butylphosphine, tri-sec-butylphosphine, tricyclopropylphosphine, tricyclohexylphosphine, triphenylphosphine, tri-p-tolylphosphine, tri-p-methoxyphenylphosphine, tri-2,4,6-trimethylphenylphosphine, phenyldiisopropylphosphine, diethylisopropylphosphine, ethyl-di-t-butylphosphine, diethyl-t-butylphosphine, ethyldicyclohexylphosphine, methylphenylbenzylphosphine, diethylphenylphosphine, ethyldiphenylphosphine, dimethylphenylphosphine and methyldiphenylphosphine, phosphines represented by the formula [II] such as trisdimethylaminophosphine, trisdiethylaminophosphine, trisdi-n-propylaminophosphine, trisdiisopropylaminophosphine, trisdi-rw butylaminophosphine, trisdiisobutylaminophosphine, trisdi-t-butylaminophosphine and trisdicyclohexylaminophosphine, phosphites represented by the formula [III] such as trimethyl phosphite, triethyl phosphite, tri-n-propyl phosphite, triisopropyl phosphite, tri-n-butyl phosphite, triisobutyl phosphite, tri-t-butyl phosphite, tricyclohexyl phosphite, triphenyl phosphite, tri-p-tolyl phosphite and tri-p-methoxyphenyl phosphite, and phosphines represented by the formula [IV] such as bisdiphenylphosphinomethane, 1,2-bisdiphenylphosphinomethane, 1,3-bisdiphenylphosphinopropane, 1,4-bisdiphenylphosphinobutane, 1,5-bisdiphenylphosphinopentane, 1,6-bisdiphenylphosphinohexane, 1,2-bisdimethylphosphinoethane, 1,2-bis-diethylphosphinoethane, 1,2-bisdicyclohexylphosphinoethane and 1,2-bispentafluorophenylphosphinoethane.

The trivalent phosphorus compounds are used usually in an amount of 0.1-100 mols, preferably in an amount of 0.1-20 mols per mol of the palladium and/or copper metal.

Examples of the lower alkanes are those of 1-4 carbon atoms such as methane, ethane, propane and butane.

The reaction is carried out in the presence of solvents. Halogenated carboxylic acids such as trifluoroacetic acid, trichloroacetic acid, monochloroacetic acid and dichloroacetic acid and halogenated hydrocarbons such as perfluorohexane are usually used as the solvents. Amount of the solvents is usually about 10-100 ml per mmol of the catalysts.

The reaction of lower alkanes with carbon monoxide is usually effected under pressure. The pressure of lower alkanes is usually about 1-50 atm. The pressure of carbon monoxide is also about 1-50 atm. The reaction temperature is usually 0°-100° C. and the reaction time is usually about 1-50 hours.

Thus, acetic acid, propionic acid, butanoic acids and pentanoic acids are produced from methane, ethane, propane and butane, respectively. After completion of the reaction, the catalysts are removed by methods familiar to the skilled and then, the desired lower carboxylic acids are recovered by distillation and the like.

According to the process of the present invention, lower carboxylic acids are easily and efficiently produced from inexpensive lower alkanes and carbon monoxide.

The present invention is explained in more detail by the following nonlimiting examples. The yield is calculated from the following formula:

Yield (%)=Amount of carboxylic acid produced (mol)/amount of catalyst metal (mol)×100

EXAMPLE 1

In an autoclave of 150 ml were charged palladium propionate (Pd(OCOC$_2$H$_5$)$_2$, 0.05 mmol), copper sulfate (1 mmol), potassium peroxodisulfate (K$_2$S$_2$O$_4$, 9 mmol), trifluoroacetic acid (5 ml) and n-perfluorohexane (2 ml). Then, methane (purity: at least 99%) of 40 atm and carbon monoxide of 20 atm were charged to give totally 60 atm.

Then, the content was heated to 80° C. and stirred for 20 hours at that temperature and thereafter cooled to room temperature. The reaction mass was analyzed by gas chromatography.

Yield of acetic acid was 1300% (based on palladium metal). No by-products were detected except a small amount of propionic acid resulting from the catalyst.

EXAMPLE 2

Example 1 was repeated except that no n-perfluorohexane was used.

Yield of acetic acid was 930% (based on palladium metal). No by-products were detected except a small amount of propionic acid resulting from the catalyst.

EXAMPLE 3

Example 2 was repeated except that propane was used in place of the methane.

Yield of butanoic acids was 660% (based on palladium metal) and the ratio of n-form/iso-form in the product was 5/6. No by-products were detected except a small amount of propionic acid resulting from the catalyst.

EXAMPLE 4

Example 1 was repeated except that no copper sulfate was used.

Yield of acetic acid was 750% (based on palladium metal). No by-products were detected except a small amount of propionic acid resulting from the catalyst.

EXAMPLE 5

Example 1 was repeated except that copper sulfate was used in an amount of 0.05 mmol is place of 1 mmol and no palladium propionate and n-perfluorohexane were used.

Yield of acetic acid was 670% (based on copper metal). No by-products were detected.

EXAMPLE 6

Example 1 was repeated except that no palladium propionate and n-perfluorohexane were used and copper sulfate (0.05 mmol), potassium peroxodisulfate (18 mmol) and trifluoroacetic acid (5 ml) were used in place of 1 mmol, 9 mmol and 5 ml, respectively, and the stirring was continued for 45 hours in place of 20 hours.

Yield of acetic acid was 4000% (based on copper metal). No by-products were detected.

EXAMPLE 7

In an autoclave of 150 ml were charged palladium acetate (Pd(OCOCH$_3$)$_2$, 0.05 mmol), copper acetate (Cu(OCOCH$_3$)$_2$, 0.1 mmol), potassium peroxodisulfate (K$_2$S$_2$O$_4$, 9 mmol) and trifluoroacetic acid (5 ml). Then, ethane of 30 atm and carbon monoxide of 20 atm were charged to give totally 50 atm.

Then, the content was heated to 80° C. and stirred for 30 hours at that temperature and thereafter cooled to room temperature. The reaction mass was analyzed by gas chromatography.

Yield of propionic acid was 8000% (based on palladium metal). No by-products were detected except a small amount of acetic acid resulting from the catalyst.

EXAMPLE 8

In an autoclave of 150 ml were charged palladium acetate (0.05 mmol), copper acetate (0.05 mmol), potassium peroxodisulfate (9 mmol) and trifluoroacetic acid (5 ml). Then, propane of 10 atm and carbon monoxide of 20 atm were charged to give totally 30 atm.

Then, the content was heated to 90° C. and stirred for 20 hours at that temperature and thereafter cooled to room temperature. The reaction mass was analyzed by gas chromatography.

Yield of butanoic acids was 7100% (based on palladium metal) and the ratio of n-form/iso-form in the product was 17/54. No by-products were detected except a small amount of acetic acid resulting from the catalyst.

EXAMPLE 9

Example 8 was repeated except that the reaction was effected at 70° C. in place of 90° C. Yield of butanoic acids was 3800% (based on palladium metal) and the ratio of n-form/iso-form in the product was 3/16. No by-products were detected except a small amount of acetic acid resulting from the catalyst.

EXAMPLE 10

Example 8 was repeated except that the reaction was effected at 60° C. in place of 90° C. Yield of butanoic acids was 2240% (based on palladium metal) and the ratio of n-form/iso-form in the product was 17/95. No by-products were detected except a small amount of acetic acid resulting from the catalyst.

EXAMPLE 11

Example 8 was repeated except that the reaction was effected after triethyl phosphite (0.15 onol) was further added. Yield of butanoic acids was 5800% (based on palladium metal) and the ratio of n-form/iso-form in the product was 11/47. No by-products were detected except a small amount of acetic acid resulting from the catalyst.

EXAMPLE 12

Example 8 was repeated except that the reaction was effected after 1,2-bisdiphenylphosphinoethane (0.075 mmol) was further added. Yield of butanoic acids was 5500% (based on palladium metal) and the ratio of n-form/ iso-form in the product was 2/13. No by-products were detected except a small amount of acetic acid resulting from the catalyst.

What is claimed is:

1. A process for producing lower carboxylic acids which comprises allowing lower alkanes to react with carbon monoxide in the presence of palladium catalysts and/or copper catalysts and salts of peroxy acids.

2. A process according to claim 1, wherein the palladium catalysts are at least one compound selected from the group consisting of acetylacetonato salts, carboxylates, oxides, halides, ammonium salts, sulfates and nitrates of palladium and coordination compounds thereof.

3. A process according to claim 1, wherein the palladium catalysts are at least one compound selected from the group consisting of $Pd(O_2CCH_3)_2$, $Pd(O_2CC_2H_5)_2$, $Pd(O_2CC_3H_7)_2$ and $PdCl_2$.

4. A process according to claim 1, wherein the copper catalysts are at least one compound selected from the group consisting of oxides, halides, hydroxides, carboxylates, sulfates, nitrates and carbonates of copper.

5. A process according to claim 1, wherein the copper catalysts are at least one compound selected from the group consisting of copper acetate and copper sulfate.

6. A process according to claim 1, wherein amount of the palladium catalysts and/or the copper catalysts is $1 \times 10^{-5} - 1 \times 10^{-1}$ mol per mol of the alkanes.

7. A process according to claim 1, wherein the salts of peroxy acids are at least one compound selected from the group consisting of salts of peroxysulfuric acid and salts of peroxyphosphoric acid.

8. A process according to claim 1, wherein amount of the salts of peroxy acids is 50–200 molar equivalent based on the catalysts.

9. A process according to claim 1, wherein the lower alkanes are at least one compound selected from the group consisting of methane, ethane, propane and butane.

10. A process according to claim 1, wherein at least one solvent selected from the group consisting of halogenated carboxylic acids and halogenated hydrocarbons is used.

11. A process according to claim 10, wherein amount of the solvents is 10–100 ml per mmol of the catalyst.

12. A process according to claim 1, wherein the reaction is carried out at a temperature within the range of 0–100° C. and under a pressure within the range of 1–100 atm.

* * * * *